(12) United States Patent
Afsari et al.

(10) Patent No.: US 9,395,291 B2
(45) Date of Patent: Jul. 19, 2016

(54) METHOD AND SYSTEM FOR GLASS PROCESSING

(71) Applicants: Farook Afsari, Menlo Park, CA (US); Kamiar Fariba, La Jolla, CA (US)

(72) Inventors: Farook Afsari, Menlo Park, CA (US); Kamiar Fariba, La Jolla, CA (US)

( * ) Notice: Subject to any disclaimer, the term of this patent is extended or adjusted under 35 U.S.C. 154(b) by 106 days.

(21) Appl. No.: 14/339,270

(22) Filed: Jul. 23, 2014

(65) Prior Publication Data

US 2016/0023248 A1  Jan. 28, 2016

(51) Int. Cl.
| | |
|---|---|
| *G06K 9/00* | (2006.01) |
| *G01N 21/25* | (2006.01) |
| *G01N 21/85* | (2006.01) |
| *B07C 5/36* | (2006.01) |
| *B07C 5/342* | (2006.01) |

(52) U.S. Cl.
CPC ............ *G01N 21/251* (2013.01); *B07C 5/342* (2013.01); *B07C 5/361* (2013.01); *G01N 21/85* (2013.01); *B07C 2501/0018* (2013.01)

(58) Field of Classification Search
CPC ..... B07B 13/18; G01N 21/251; G01N 21/892
See application file for complete search history.

(56) References Cited

U.S. PATENT DOCUMENTS

| | | | | |
|---|---|---|---|---|
| 5,314,071 | A | | 5/1994 | Christian et al. |
| 6,137,074 | A | * | 10/2000 | Doak ............... B07C 5/3425 209/581 |
| 6,901,167 | B2 | * | 5/2005 | Herley ............. G06T 7/0083 382/199 |
| 7,058,224 | B2 | * | 6/2006 | Herley ............. G06T 7/0083 382/199 |
| 7,351,929 | B2 | | 4/2008 | Afsari et al. |
| 7,355,140 | B1 | * | 4/2008 | Afsari .............. B07C 5/3425 209/576 |
| 7,383,695 | B2 | | 6/2008 | Lehman et al. |
| 7,386,997 | B2 | | 6/2008 | Lehman et al. |
| 8,436,268 | B1 | * | 5/2013 | Afsari .............. B07C 5/342 209/576 |
| 8,631,668 | B2 | | 1/2014 | Duffy et al. |
| 2005/0242006 | A1 | * | 11/2005 | Bohlig ............. B03B 9/061 209/659 |
| 2008/0061125 | A1 | * | 3/2008 | Langlois .......... G06Q 50/28 235/376 |

* cited by examiner

*Primary Examiner* — Shefali Goradia

(74) *Attorney, Agent, or Firm* — Squire Patton Boggs (US) LLP

(57) ABSTRACT

A mixture of glass pieces can be evaluated by taking an image of an object from the mixture. The object has the possibility of being either a single piece of glass from the mixture or at least two pieces of glass from the mixture. By knowing how many pieces of glass are in each object, the accuracy of the evaluation can be improved. Angles of an outline of the object are determined from the image, and then the angles are evaluated to determine whether the object is at least two pieces. When it is determined that the objection is at least two pieces, it is possible to assign a characteristic, such as color type or material type, for each piece as opposed to assigning the same characteristic to the entire object.

24 Claims, 4 Drawing Sheets

METHOD AND SYSTEM FOR GLASS PROCESSING

FIELD OF THE INVENTION

This invention relates generally to a method and system for evaluating a mixture containing colored objects, and more particularly, for evaluating the purity of cullet.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Glass containers are 100% recyclable and can be recycled endlessly without any loss in purity or quality. Over a ton of natural resources are saved for every ton of glass recycled. Energy costs drop about 2-3% for every 10% cullet (post-consumer glass) used in the manufacturing process. Glass furnace life is increased by 10% when recycled glass is used in the production of new glass containers. One ton of carbon dioxide is reduced for every six tons of recycled container glass used in the manufacturing process.

Although glass container manufacturers are able to use as much as 95% recycled glass in the manufacturing process, glass container manufacturers often use only about 35% recycled glass. When using recycled glass as feedstock to manufacture new glass containers, energy costs of glass container manufacturers can be 15% less, emissions can be reduced by 20%, and furnace life can be extended by 10%. Glass container manufacturers prefer to use all the recycled furnace-ready cullet they can procure. A significant barrier to this is the quality of recycled glass available and assurance that the cullet receive is furnace-ready cullet, which must be high purity clean and color-sorted. With contaminated cullet, the reject rate in the manufacture of new glass containers increases, which increases the cost of manufacturing new glass containers. Even one small contaminant in a manufactured bottle can result in rejection.

Consumers place their recyclables by their curb side, which is picked up by hauling companies and taken to a Material Recovery Facility (MRF) where the various recyclables are sorted out and the residual, which is a mixture having high glass content, is sent to Glass Processors to be cleaned, color sorted and then sold as cullet to glass container manufacturers for use in producing new glass containers.

In years past, consumers had to place recyclables in different bins by their curb side. However, in order to reduce the cost of recycling and increase the amount that is recycled, cities have since transitioned to "single stream collection" whereby all recyclables are placed in a single bin. With single stream collection, Material Recovery Facilities (MRFs) have to deal with co-mingled material. While MRFs remove larger pieces of paper, most of aluminum cans and plastic containers, their residue and what they are unable to remove, comes out of their facilities with a large percentage of broken glass, typically as three-color (clear, brown, green) mixed dirty glass. So glass is part of this residual that MRFs send to glass processors, hence the glass is mixed with a lot of other material which is considered to be contaminants. The glass processors receive this as their raw material feedstock, which can contain as much as 40 to 50% contaminant (non-glass). However, the furnace-ready cullet which glass processors are required to provide to glass container manufacturers must contain less than 0.001% contaminant or almost 100% clean color sorted glass. The quality of cullet is the most important factor for glass container manufacturers.

While producing quality cullet is important, the ability to test the cullet is crucial. Today glass processors use manual methods to test the quality of the cullet that is delivered to them. A material sample, usually 50 lbs, is spread on a work table, a quality inspection person manually separates the contents of the sample, weighs each content group, fills out a sheet of paper with data which is compared to the specification of the glass container manufacturer (or other end user) to determine if the cullet delivery passes or fails to meet specifications. This manual process can take up to 45 minutes for each sample. The samples have to be tested several times a day and for each truck shipment, adding high labor cost to the end product. Accordingly, there is a need for efficient and accurate method and system for testing the quality of cullet.

SUMMARY

Described herein are a method and system for glass processing.

Various aspects of the invention are directed to a method comprises taking an image of an object from the mixture, the object possibly being either a single piece from the mixture or at least two pieces from the mixture. The method further comprises determining, from the image, angles of an outline of the object. The method further comprises evaluating the angles to determine whether the object is at least two pieces, and evaluating a characteristic of the object.

Various aspects of the invention are directed to a system comprises an imaging device configured to take an image of an object from the mixture, the object possibly being either a single piece from the mixture or at least two pieces from the mixture. The system further comprises a light source configured to direct light toward the imaging device. The system further comprises a processor configured to determining, from an image taken by the imaging device, angles of an outline of the object. The processor is further configured to evaluate the angles to determine whether the object is at least two pieces and to evaluate a characteristic of the object.

Various aspects of the invention are directed to a non-transitory computer readable medium having a stored computer program embodying instructions, which when executed by a computer, causes the computer to evaluate a mixture including a plurality glass pieces. The computer readable medium comprises instructions to take an image of an object from the mixture, the object possibly being either a single piece from the mixture or at least two pieces from the mixture. The computer readable medium further comprises instructions to determine, from the image, angles of an outline of the object instructions to evaluate the angles to determine whether the object is at least two pieces, and instructions to evaluate a characteristic of the object.

Various aspects of the invention are directed to a method comprising taking an image of an object from the mixture, the object having the potential of being either a piece of glass with label or a piece of glass without a label. The method further comprises determining, from the image, angles of an outline of the object. The method further comprises detecting, from the image, a light transmittance boundary line within the outline of the object, the light transmittance boundary line having an endpoint on the outline. The method further comprises identifying the object as a piece of glass with a label based, at least, on the angle of the outline at the endpoint of the light transmittance boundary.

The features and advantages of the invention will be more readily understood from the following detailed description which should be read in conjunction with the accompanying drawings.

DETAILED DESCRIPTION OF EXEMPLARY EMBODIMENTS

Figure 1:
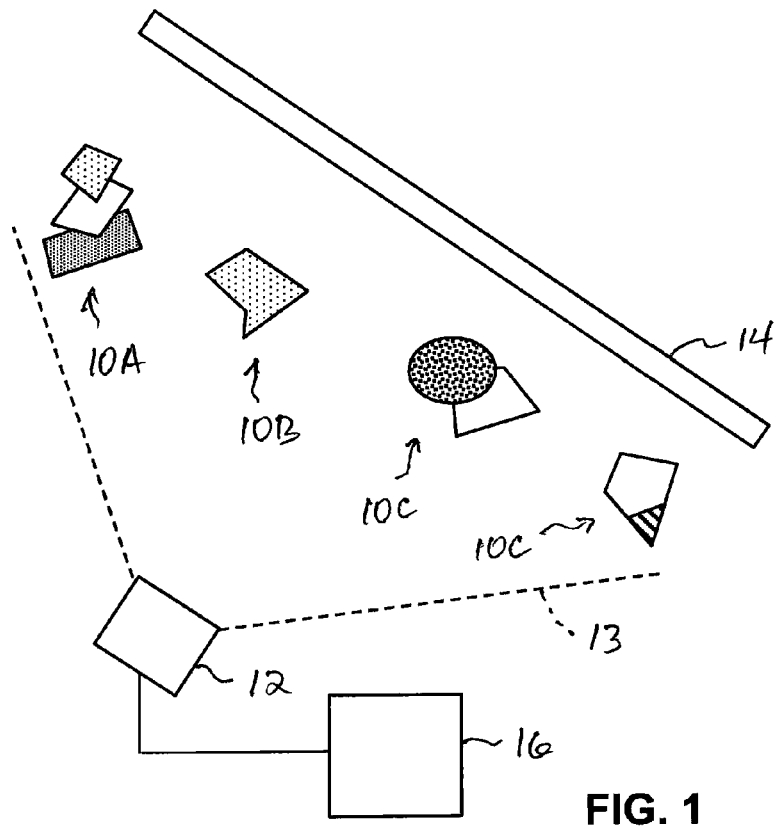
FIG. 1 is a schematic view of an exemplary system, showing an imaging device, processor coupled to the imaging device, a light source, and a plurality of objects to be examined.

Referring now in more detail to the exemplary drawings for purposes of illustrating embodiments of the invention, wherein like reference numerals designate corresponding or like elements among the several views, there is shown in FIG. 1 a plurality of objects 10A-10D disposed between imaging device 12 and light source 14. Imaging device 12 is configured to take an image of all objects 10A-10D simultaneously, or optionally take an image of only one or a limited number of the objects.

Objects 10A-10D are samples obtained from a mixture that includes many pieces of glass and non-glass debris material. The mixture can be residual material from a Material Recovery Facility (MRF). The mixture can be cullet produced by a glass processor which sorts residual material from the MRF. The mixture can be cullet received by a glass manufacturer for making new glass containers.

The glass pieces in the mixture can belong to various color types. Color types include without limitation clear (or flint), amber (or brown), and green. The non-glass debris material can be ceramic plastic, metal, wood, stone, or rock. The mixture can be a cullet mixture resulting from a prior process which attempted to separate glass pieces by color type. Additionally or alternatively, the mixture can be the result of a prior sorting process which attempted to remove non-glass debris material. The method and system described herein can be used to verify quality of the sorting process. For example, method and system can test whether a cullet mixture satisfies a predetermined requirement, such as 95% amber glass by weight and/or less than 5% non-glass debris material by weight. As another example, the predetermined requirement can be 98% clear glass by weight and/or less than 2% non-glass debris material by weight. Additionally or as an alternative to use after a sorting process, the method and system described herein can be used during the sorting process to help ensure that the resulting cullet mixture satisfies predetermined requirements.

In FIG. 1, four objects (10A-10D) are simultaneously within field of view 13 of imaging device 12. It is possible for there to be a greater or lesser number of objects within field of view 13 than what is illustrated. As discussed below, any one of the four objects (10A-10D) can in fact be multiple items. A system and method will be described for determining whether or not any of the objects (10A-10D) comprises multiple items.

Light source 14 is configured to direct light toward objects 10A-10D. The type of light includes visible light. Light source 14 is oriented such that an outline each of the objects can be detected by the imaging device 12. Light source 14 includes any one or a combination of a mirror, a light guide, and a light generator such as a light bulb or light emitting diode (LED). The light directed by light source 14 allows imaging device 12 to determine the composition and characteristics of objects 10A-10D. Characteristics includes without limitation color type and material type. Color type includes without limitation clear (or flint), amber (or brown), and green. Material type includes without limitation glass versus non-glass debris material.

Imaging device 12 can include one or more electronic sensors configured to detect the intensity and color of light passing through objects 10A-10D and at the edges of objects 10A-10D. Electronic sensors include without limitation charge-coupled devices (CCD) and complementary metal-oxide-semiconductors (CMOS). Imaging device 12 is coupled to processor 16. Processor 16 includes one or more integrated circuits for evaluating images from the imaging device 12 and one or more memory components for storing the images.

Figure 2:
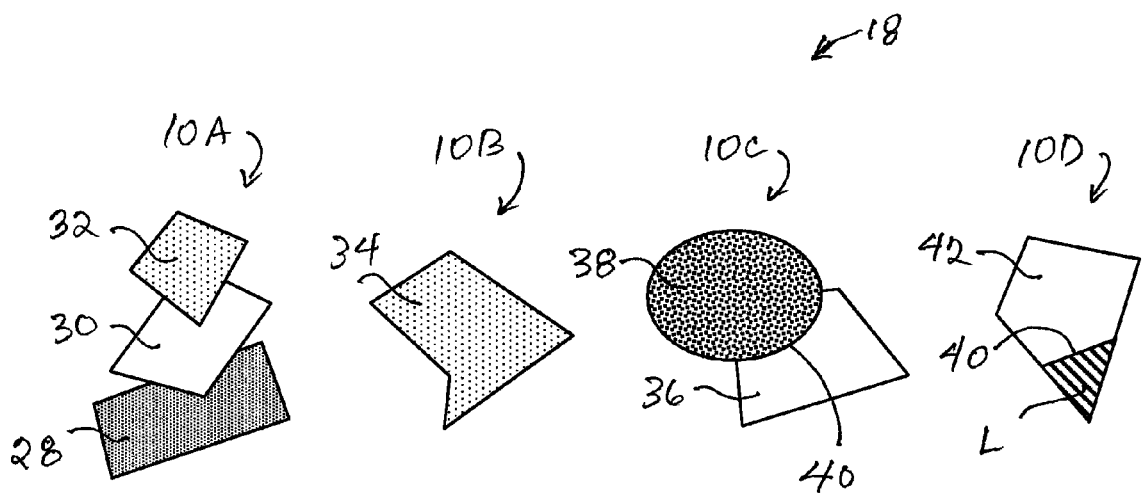
FIG. 2 is a simulated image of the objects taken by the imaging device and communicated to the processor.

FIG. 2 shows image 18 taken by imaging device 12. Image 18 is stored and evaluated by processor 16. Each of the objects 10A-10D can actually be one or more pieces of glass and/or non-glass debris material. In the illustration, object 10A consists of three overlapping pieces of glass, object 10B consists of a single piece of glass, object 10C consists of one piece of glass and one piece of non-glass debris material, and object 10D consists of a single piece of glass with a label. The illustrated composition for the objects is exemplary and is not intended to limit the invention. Other combinations for each object are possible, such as: two pieces of glass with labels; two pieces of glass with labels and one piece of non-glass debris material; one piece of glass with a label, two pieces of glass without a label, and a piece of non-glass debris material; and so on.

Processor 16 is configured to determine the composition of each one of the objects (10A-10D) by analyzing image 18. The composition refers to the number of items present or contained in each object. By determining the composition of each object, it is possible to characterize the object more accurately and thereby enable a more accurate quality test of whether a cullet mixture meets predetermined requirements or enable more accurate sorting to ensure that the resulting cullet mixture meets the predetermined requirements. Without a determination of composition, object 10A could be mistakenly characterized as a single piece of amber glass when in fact it consists of one piece of amber glass, one piece of clear glass, and one piece of green glass. As a further example, object 10C could be mistakenly characterized as single of piece of desired glass when in fact it consists of one piece of desired glass and one piece of undesirable debris material. In yet another example, object 10D could be mistakenly characterized as a single piece of undesirable debris material when it is a piece of desired glass with a label adhered to it. These potential inaccuracies can be avoided by analyzing image 18 to determine the composition of one or more of the objects.

Figure 3:
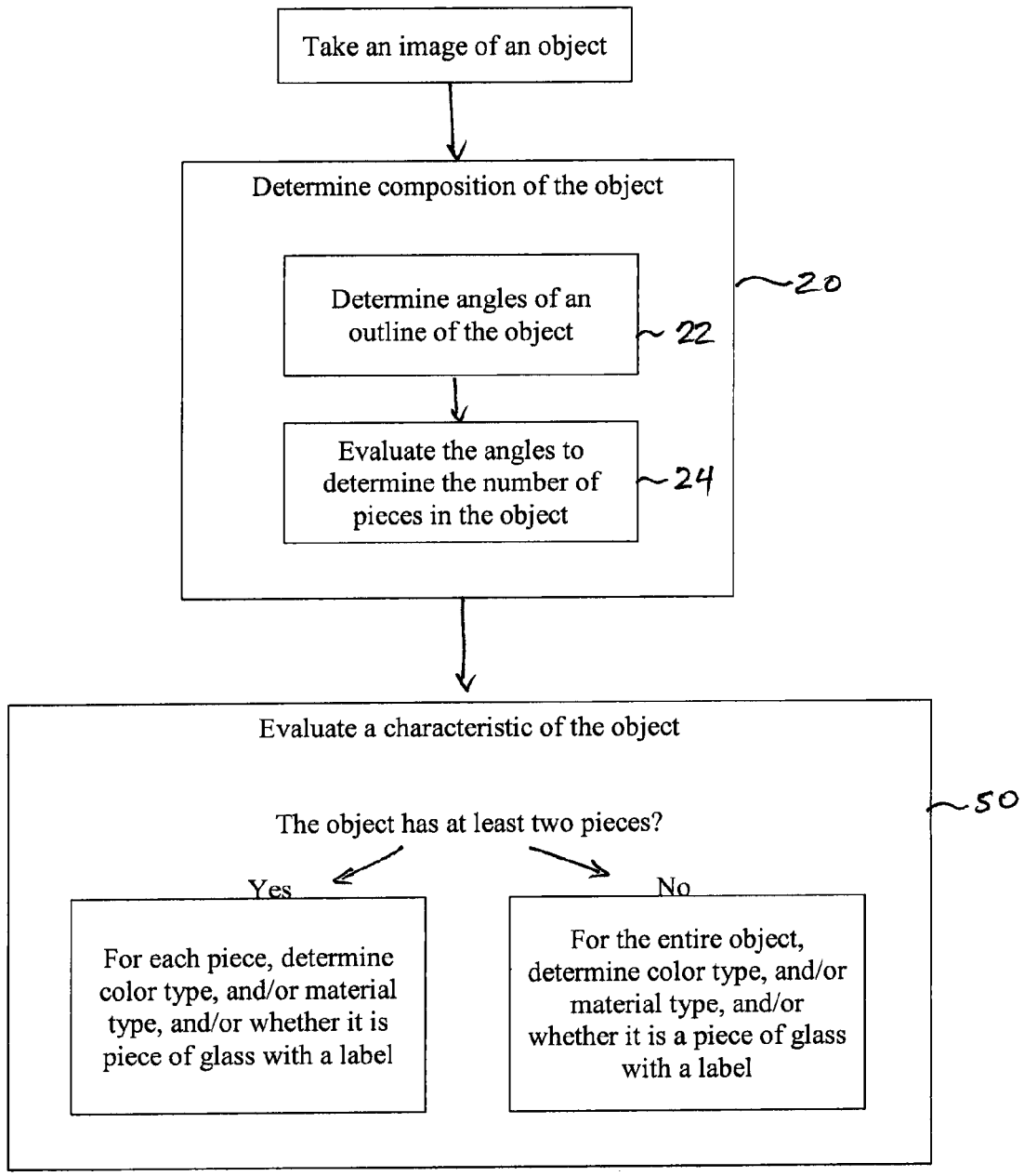
FIG. 3 is a block diagram showing an exemplary method.

In some embodiments, as shown in FIG. 3, the determination of composition (block 20) of the objects (10A-10D) includes determining, from image 18, angles of an outline of the object (block 22). Next, angles are evaluated (block 24) to determine whether each of the objects contains at least two pieces.

Figure 4:
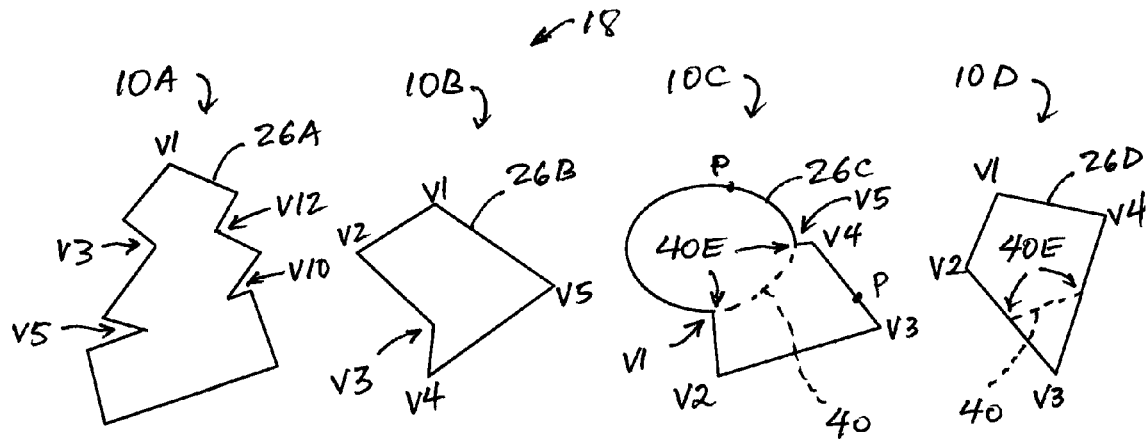
FIG. 4 is a diagram showing object outlines obtained from the image of FIG. 2.

Referring to FIG. 4, the determination of angles (block 22) is performed by obtaining an outline of each of the objects (10A-10D). The outline refers to edges of the object which define an area of image 18 occupied by the object. In FIG. 4, only outlines 26A-26D of the objects are illustrated. Other details of image 18 in FIG. 2 (such as indicators of color type, opacity, and where pieces overlap) are omitted from FIG. 4 to clarify the discussion below. Each of the outlines 26A-26D includes one or more vertices. As discussed below, angles at each of the vertices can be used to determine the number of pieces in each object.

Figure 5:
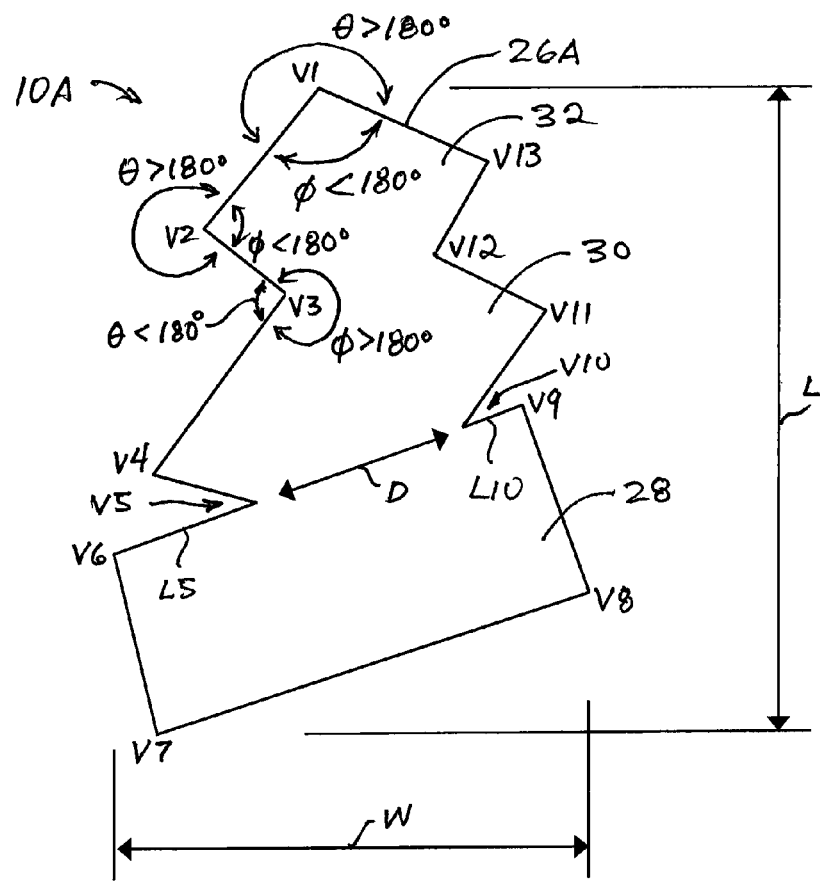
FIG. 5 is a detailed view of the object outline of one of the objects in FIG. 4.

FIG. 5 shows a detailed view of outline 26A of object 10A. Outline 26A includes vertices V1 to V13. The interior angle Φ at each of the vertices is compared to a threshold value. For example, the threshold value can be 180 degrees, and processor 16 determines whether a vertex has an interior angle Φ greater than 180 degrees. Results of the comparison are shown in TABLE I.

TABLE I

| Vertex | Does interior angle Φ violate threshold? |
|---|---|
| V1 | No |
| V2 | No |
| V3 | YES (suspect vertex) |
| V4 | No |
| V5 | YES (suspect vertex) |
| V6 | No |
| V7 | No |
| V8 | No |
| V9 | No |
| V10 | YES (suspect vertex) |
| V11 | No |
| V12 | YES (suspect vertex) |
| V13 | No |

The interior angle Φ of outline 26A is greater than the threshold value of 180 degrees at vertices V3, V5, V9, and V12. A vertex which violates the threshold (e.g., has an interior angle Φ greater than 180 degrees) represents either a stress concentration that could result in the piece of glass breaking apart into more pieces or an intersection between two pieces of glass. For convenience of discussion, a vertex which violates the threshold is referred to as a suspect vertex. The threshold value is selected such that a suspect vertex is more likely to represent an intersection between two separate pieces. The threshold value of 180 degrees is selected to provide confidence that a suspect vertex most probably represents an intersection between two separate pieces, as opposed to representing a single piece of glass with a stress concentration. Other threshold values for the interior angle Φ can be selected, such as 185 degrees, 190 degrees, 195 degrees, 200 degrees, 205 degrees, and so on. The threshold value can be a value in the range of 180 degrees to 205 degrees, for example. In general, a greater threshold value can provide greater confidence that a suspect vertex truly represents an intersection between two separate pieces.

In some embodiments, the angle which is determined in block 22 of FIG. 3 is the exterior angle θ. For the exterior angle θ, the threshold angle is used in reverse. That is, a vertex is identified as a suspect vertex when its exterior angle θ is less than the threshold of 180 degrees. Other threshold values for the exterior angle θ can be selected, such as 185 degrees, 190 degrees, 195 degrees, 200 degrees, 205 degrees, and so on.

In some embodiments, a suspect vertex is paired with another suspect vertex as a condition to concluding that the two suspect vertices represent an intersection between two separate pieces. In FIG. 5, processor 16 determines that leg L5 of vertex V5 is aligned with leg L10 of vertex V10. Due to alignment of legs, processor 16 identifies vertices V5 and V10 as a suspect vertex pair and as an intersection between two separate pieces 28 and 30. Alignment is found when legs L5 and L10 are on the same imaginary line (i.e., legs L5 and L10 are collinear) or when legs L5 and L10 form an angle that is less than an alignment threshold angle. The alignment threshold angle can be, for example, any one of 2 degrees, 4 degrees, 6 degrees, 8 degrees, 10 degrees, and so on.

Additionally or alternatively, processor 16 determines vertices V5 and V10 are in sufficient proximity to each other as a condition to concluding that the two suspect vertices represent an intersection between two separate pieces. Due to sufficient proximity, processor identifies vertices V5 and V10 as a suspect vertex pair and as an intersection between two separate pieces 28 and 30. Sufficient proximity is found when the distance D between vertices V5 and V10 is within a threshold distance. The threshold for distance D can be an absolute distance. The absolute distance can be, for example, any one of 5 mm, 1 cm, 2 cm, 3 cm, 4 cm, and so on. The threshold for distance D can be a percentage of another dimension taken from outline 26A. For example, the threshold for distance D can be a percentage (such as 50%, 100%, 150%, or 200%) of a leg (such as L5 or L10) adjacent to a suspect vertex. As a further example, the threshold for distance D can be a percentage (such as 50%, 25%, 10%, or 5%) of an overall length L or width W of the object.

In the foregoing examples, pairing of suspect vertices V5 and V10 is based on a predetermined criteria, such alignment and/or proximity. In addition or alternatively, other criteria can be used, such as similarity in the curvature of legs adjacent to the suspect vertices (e.g., legs L5 and L10), similarity in image pixel color of legs adjacent to the suspect vertices, and/or presence of a light transmittance boundary line at the suspect vertices. Light transmittance boundary lines 40 are described below.

Optionally, other suspect vertices can be paired by a process of elimination. For example, after suspect vertices V5 and V10 are paired in object 10A, the only remaining suspect vertices are V3 and V12. In this situation where there are exactly two remaining suspect vertices, suspect vertices V3 and V12 are automatically identified by processor 16 as a suspect vertex pair and as an intersection between two separate pieces 30 and 32 (FIG. 2).

Referring to FIG. 4, outline 26B of object 10B has only one suspect vertex. That is, outline 26B has only one vertex (V3) having an interior angle Φ that is greater than the threshold or an exterior angle θ that is less than the threshold. In some embodiments, since the total number of suspect vertices for object 10B is exactly one, processor 16 identifies that vertex (V3) as not being an intersection between two separate pieces. Processor 16 concludes that object 10 consists of a single piece 34 (FIG. 2).

On the other hand, outline 26C of object 10C has exactly two suspect vertices. That is, vertices V1 and V5 each have an interior angle Φ that is greater than the threshold or an exterior angle θ that is less than the threshold. In some embodiments, since the total number of suspect vertices for object 10C is exactly two, processor 16 identifies those vertices (V1 and V6) as a suspect vertex pair and as an intersection between two separate pieces 36 and 38 (FIG. 2).

In object 10C, piece 36 is actually a piece of translucent glass, and piece 38 is actually a piece of opaque, non-glass debris material. This composition can be determined by processor 16 as follows. The opacity of piece 38 results in light transmittance boundary line 40 (FIG. 4) within outline 26C. The light transmittance boundary line 40 can arise when, for example, no light or very little light passes through the opaque, non-glass debris material. Processor 16 detects light transmittance boundary line 40 as an abrupt change in light intensity passing through object 10C captured in image 18. Light transmittance boundary line 40 has endpoints 40E at suspect vertices V1 and V5. Additionally or alternatively, since endpoints 40E are located at suspect vertices V1 and V5, processor 16 identifies those vertices (V1 and V5) as a suspect vertex pair and as an intersection between two separate pieces 36 and 38 (FIG. 2) and does not mistakenly identify piece 36 as a piece of glass with a label. Further evaluation by processor 16, as described below, will reveal piece 36 as a piece of glass and piece 38 as non-glass debris material.

Referring again FIG. 4, outline 26D of object 10D has no suspect vertex. That is, none of vertices V1 to V5 have an interior angle Φ that is greater than the threshold or an exterior angle θ that is less than the threshold. In some embodiments, since the total number of suspect vertices for object 10D is exactly zero, processor 16 concludes that object 10D consists of a single piece 42 (FIG. 2). Piece 42 is actually a single piece of glass with a label L, as shown in FIG. 2. This can be determined by processor 16 as follows. Label L is a piece of paper, opaque plastic, or foil which is adhered on the surface of piece 42. Label L results in light transmittance boundary line 40. The light transmittance boundary line 40 can arise when, for example, no light or very little light passes through label L. Processor 16 determines that endpoints 40E of light transmittance boundary line 40 are not located at any suspect vertex. Additionally or alternatively, since endpoints 40E are not located at any suspect vertex, processor 16 concludes that object 10D consists of a single piece of glass 42 with label L and does not mistakenly conclude that object 10D contains a piece of non-glass debris material.

Referring again to FIG. 3, the characteristic of the object can be determined (block 50) after the composition of the object has been determined (block 20). As described above, when processor 12 concludes that the object is a single piece of material, it can deduce that the single piece is a piece of glass with a label based, at least, on the presence of a light transmittance boundary line within the outline of the object. To evaluate other characteristics, processor 12 analyzes image 18 to determine, for each piece contained within the object, color type, material type, and/or whether the piece is a piece of glass with a label.

After concluding that object 10A consists of three pieces, processor 12 determines areas of possible overlap that might lead of inaccurate analysis. The areas of possible overlap are areas between suspect vertex pair V5, V10 and between suspect vertex pair V3, V12 (FIG. 5). In some embodiments, processor 12 analyzes areas of image 18 adjacent to a vertex which is not a suspect vertex. For example, processor can analyze image areas adjacent to vertices V6, V4, and V2 to determine the color type of each of glass pieces 28, 30, and 32 respectively.

Additionally or alternatively, after concluding that object 10C consists of two pieces, processor 12 analyzes areas of image 18 adjacent to points P on the outline and located at a distance away from suspect vertex pair V1, V5 (FIG. 4). Selection of areas at a distance away from suspect vertices V1 and V5 can help avoid areas of possible overlap that could lead of inaccurate analysis.

After the composition (i.e., number of items) of each object is determined, the characteristics (e.g., color type, presence of non-glass debris, and presence of labels adhered to glass) of individual pieces in each object can be determined using system and methods known in the art, in addition to or as alternatives to the methods described above. See, for example, U.S. Pat. No. 5,314,071 issued to Christian et al., entitled "Glass Sorter."

Imaging device 12, processor 16, and light source 14 can be implemented to perform quality tests on the cullet output of a glass sorter.

Figure 6:
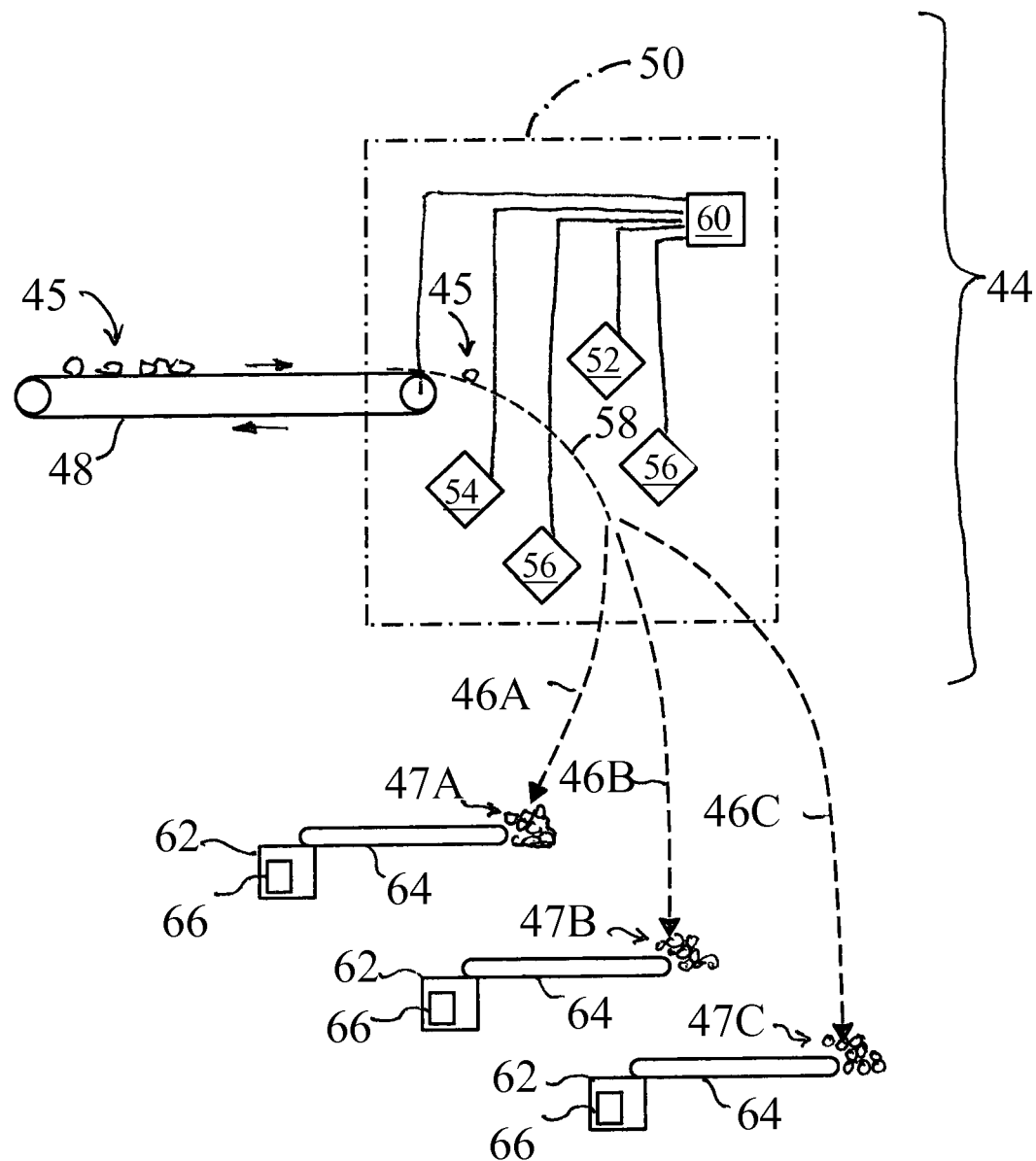
FIG. 6 is a schematic view of an exemplary system, showing a glass sorter and quality test modules.

In FIG. 6, glass sorter 44 is configured to sort a mixture of glass pieces 45 by color type and eject a separate cullet output stream 46A, B, C for each glass color type. For example cullet output stream 46A can be a stream of green cullet, output stream 46B can be a stream of amber (or brown) cullet, and output stream 46C can be a stream of clear (or flint) cullet. Glass sorter 44 includes conveyor belt 48 which transports the mixture of glass pieces 45 to sorting assembly 50.

Sorting assembly 50 produces output streams 46A, B, C. Sorting assembly 50 includes sensor modules 52 and light modules 54 directed toward sensor modules 52. Sensor modules 52 are used to determine the color type of the glass pieces which fall from the edge of conveyor belt 48. Sorting assembly 50 includes actuators 56 controlled by control module 60 which is communicatively coupled to conveyor belt 48, sensor modules 52, and light modules 54. Actuators 56 can be pneumatic blowers, mechanical gates, or electrostatic plates. Actuators 56 are configured to push or guide selected glass pieces into a selected one of the output streams 46A, B, C based upon analysis of data from sensor modules 52 by control module 60. In the illustrated embodiment, sensor modules 52 are located above free-fall trajectory 58 of mixed glass material 45. The number, arrangement and orientation of sensor modules 52, light modules 54, and actuators 56 can be different from what is illustrated. The sensor modules, light modules, and actuators can be as described in U.S. Pat. No. 7,351,929, U.S. Pat. No. 7,355,140, or U.S. Pat. No. 8,436,268. The entirety or a portion of glass sorter 44 can be as described in U.S. Pat. No. 5,314,071.

Tests on the quality of the cullet output of glass sorter 44 (FIG. 6) can be performed using quality test modules 62 which are configured to determine the composition and characteristics of objects as described in connection with FIGS. 1-5. Transporters 64 move cullet from each of output streams 46A, B, C to quality test modules 62. Each transporter 64 can be a conveyor belt, a rotating feed wheel, a pivoting diverter plate, or similar device. Each quality test module 62 includes imaging device 12, processor 16, and light source 14 previously described (see FIGS. 1-5). Each transporter 64 slides or drops cullet pieces (for example, objects 10A-10D in FIG. 1) between imaging device 12 and light source 14. Processor 16 provides an indication of the purity of the cullet. For example, processor 16 can indicate that the amber cullet output from glass sorter 44 satisfies or fails to satisfy a predetermined quality requirement, such as at least 95% amber glass by weight. As another example, the predetermined quality requirement can be that any of the cullet output must be less than 2% non-glass debris material by weight with the remainder being at least 95% by weight of the desired color type. Each quality test module 62 optionally includes output module 66 which provides the indication of purity. Output module 66 can be a display screen or printer that shows the purity level. Alternatively, output module 66 can be an audio or visual alarm configured to automatically alert the person who is operating glass sorter 44.

In the illustrated embodiment, there are three quality test modules 62. One quality test module 62 is dedicated for each cullet collection area 47A, B, C. In other embodiments, sorter 44 is configured to sort more than three color types and output a corresponding number of cullet output streams. There can be a separate quality test module for each cullet collection area. Alternatively, there can be only one quality test module which is movable between various cullet collection areas.

In FIG. 6, the quality test modules 62 are shown at fixed locations at the end of each cullet output streams. In other embodiments, there is no quality test module at a fixed location. For example, there can be a quality test module that is stored at a location away from the cullet output streams. When needed, a sample quantity can be taken from a cullet output stream and then carried by a person to quality test module so that a quality test can be performed.

In some embodiments, one or more of the quality test modules 62 are communicatively coupled to control module 60 of glass sorter 44. Control module 60 is configured to alter the operation of glass sorter 44 based on output signals from quality test module 62. For example, if the predetermined quality requirement is not met, processor 16 within quality test module 66 automatically causes control module 60 to stop conveyor belt 48 and other machinery in glass sorter 44 to allow for maintenance or adjustments to the machinery. As another example, if the predetermined quality requirement is not met, processor 16 within quality test module 66 automatically causes control module 60 to change one or more glass sorter parameters to increase the purity level of the cullet. Glass sorter parameters include without limitation the speed of conveyor belt 48, the rate at which mixed glass is place onto conveyor belt 48, and settings for suctioning and/or filtering out non-glass debris from the mixture of glass material 45.

In some embodiments, one or more of the quality test modules 62 are configured or programmed to performed the above-described tests on the quality of cullet at random times or at fixed time intervals. In the case of fixed time intervals, tests can be performed every 5 minutes, or every 10 minutes, or every 30 minutes, or other time duration. In the case of testing at random times, the time interval between tests is not fixed, and the time intervals of many tests can be specified to provide an average time interval. For example, tests can be performed randomly such a first time interval is 32 minutes, followed by a second time interval of 15 minutes, and followed by a third time interval of 18 minutes, and so on, such that all time intervals result in an average time interval. The average time interval between tests is 5 minutes, 10 minutes, 30 minutes, or other time duration. Optionally, one or more of the quality test modules 62 are further configured or programmed such that, when the predetermined quality requirement is not met, the quality test modules 62 automatically increase the frequency of testing. For example, the quality test module 62 may automatically reduce the fixed time interval or the average time interval. Increasing the frequency of testing provides a greater number of data points for characterizing the quality of the cullet.

Additionally or alternatively, one or more of the quality test modules 62 are configured or programmed such that, when the predetermined quality requirement has been met and exceeded, the quality test module 62 automatically decreases the frequency of testing. For example, the quality test module 62 may automatically increases the fixed time interval or the average time interval.

In some embodiments, sorting assembly 50 can determine the composition and characteristics of objects as described in connection with FIGS. 1-5. For example, imaging device 12, processor 16, and light source 14 (all of which were described in connection with FIGS. 1-5) can be implemented to perform sorting within sorting assembly 50 of glass sorter 44. Within sorting assembly 50, sensor modules 52 can include or be replaced with imaging devices 12, light modules 52 can include or be replaced with light sources 14, and control module 60 can include or be replaced with processor 16.

In some embodiments, there are one or more memory components which form a computer readable medium. The computer readable medium may be volatile or non-volatile. Examples of a computer readable medium include without limitation a magnetic storage device (e.g., computer hard drives), an optical storage device (e.g., a CD-ROM and DVD-ROM), or a flash memory device (e.g., memory cards and USB flash drives). Processor 16 and/or control module 60 may include the computer readable medium. Alternatively, processor 16 and/or control module 60 may be communicatively coupled to another device capable of reading the computer readable medium.

The computer readable medium has a stored computer program embodying instructions, which when executed by a computer (e.g., processor 16 and/or control module 60, or other computer) causes the computer to evaluate a mixture of glass pieces according to the process steps described herein, including process steps described in connection with any of FIGS. 1-6. The computer readable medium includes instructions for performing the process steps described herein, including process steps described in connection with any of FIGS. 1-6.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for evaluating a mixture including a plurality glass pieces, the method comprising:
    taking an image of an object from the mixture, the object possibly being either a single piece from the mixture or at least two pieces from the mixture;
    determining, from the image, angles of an outline of the object;
    evaluating the angles to determine whether the object is at least two pieces;
    evaluating a characteristic of the object;
    detecting, from the image, a light transmittance boundary line within the outline of the object, the light transmittance boundary line having an endpoint on the outline;
    evaluating a position of an endpoint on the outline to determine whether the light transmittance boundary line is present on a single piece of the mixture; and
    identifying the single piece of the mixture as a piece of glass with a label when the light transmittance boundary line is determined to be present on a single piece of the mixture.

2. The method of claim 1, wherein the evaluating of the angles includes determining whether interior angles of vertices of the outline are greater than a threshold or determining whether exterior angles of the vertices are less than the threshold.

3. The method of claim 2, wherein the threshold is 180 degrees.

4. The method of claim 1, wherein the object is determined to be at least two pieces when the outline includes at least two vertices each having an interior angle greater than a threshold or an exterior angle less than the threshold.

5. The method of claim 4, wherein the object is determined to be at least two pieces when the at least two vertices are paired according to a predetermined criteria.

6. The method of claim 5, the predetermined criteria is selected from the group consisting of alignment of legs adjacent to the at least two vertices, proximity of the at least two vertices, similarity in the curvature of legs adjacent to the at least two vertices, similarity in image pixel color of legs adjacent to the at least two vertices, and/or presence of a light transmittance boundary line at the at least two vertices.

7. The method of claim 1, wherein when the object is determined to be at least two pieces, the evaluating of the characteristic of the object includes determining from the image whether a first piece of the object has a characteristic that is different from that of a second piece of the object.

8. The method of claim 7, wherein the characteristic includes color type.

9. The method of claim 7, wherein the characteristic includes material type.

10. The method of claim 1, wherein when the object is determined not to be at least two pieces, the evaluating of the characteristic of the object includes determining, from the image, a color type of the object.

11. The method of claim 1, wherein when the object is determined to not include at least two pieces, the evaluating of the characteristic of the object includes determining, from the image, a material type of the object.

12. The method of claim 1, further comprising:
evaluating the position of an endpoint of the light transmittance boundary line on the outline to determine whether the light transmittance boundary line represents an intersection between two pieces of the mixture; and
identifying the two pieces of the mixture as being a piece of glass and a piece of non-glass debris when the light transmittance boundary line is determined to represent an intersection between the two pieces of the mixture.

13. The method of claim 1, further comprising determining, by use of a processor, whether the mixture satisfies a predetermined requirement, wherein the predetermined requirement includes any one or both of a maximum amount of non-glass debris and a minimum amount glass having a desired color type.

14. A method for evaluating a mixture including a plurality glass pieces, the method comprising:
taking an image of an object from the mixture, the object possibly being either a single piece from the mixture or at least two pieces from the mixture;
determining, from the image, angles of an outline of the object;
evaluating the angles to determine whether the object is at least two pieces;
evaluating a characteristic of the object;
determining, by use of a processor, whether the mixture satisfies a predetermined requirement, wherein the predetermined requirement includes any one or both of a maximum amount of non-glass debris and a minimum amount glass having a desired color type; and
automatically changing one or more parameters of a glass sorter from which the mixture was obtained, wherein the one or more parameters are changed based, at least, on the determination of whether the mixture obtained from the glass sorter satisfies the predetermined requirement.

15. The method of claim 14, further comprising
detecting, from the image, a light transmittance boundary line within the outline of the object, the light transmittance boundary line having an endpoint on the outline;
evaluating a position of an endpoint on the outline to determine whether the light transmittance boundary line is present on a single piece of the mixture; and
identifying the single piece of the mixture as a piece of glass with a label when the light transmittance boundary line is determined to be present on a single piece of the mixture.

16. A method for evaluating a mixture including a plurality glass pieces, the method comprising:
taking an image of an object from the mixture, the object possibly being either a single piece from the mixture or at least two pieces from the mixture;
determining, from the image, angles of an outline of the object;
evaluating the angles to determine whether the object is at least two pieces;
evaluating a characteristic of the object;
determining, by use of a processor, whether the mixture satisfies a predetermined requirement, wherein the predetermined requirement includes any one or both of a maximum amount of non-glass debris and a minimum amount glass having a desired color type; and
automatically changing frequency of testing based, at least, on the determination of whether the mixture obtained from the glass sorter satisfies the predetermined requirement.

17. A system for evaluating a mixture including a plurality glass pieces, the system comprising:
an imaging device configured to take an image of an object from the mixture, the object possibly being either a single piece from the mixture or at least two pieces from the mixture;
a light source configured to direct light toward the imaging device; and
a processor configured to determining, from an image taken by the imaging device, angles of an outline of the object, the processor further configured to evaluate the angles to determine whether the object is at least two pieces and to evaluate a characteristic of the object,
wherein the processor is further configured to:
detect, from the image, a light transmittance boundary line within the outline of the object, the light transmittance boundary line having an endpoint on the outline;
evaluate a position of an endpoint on the outline to determine whether the light transmittance boundary line is present on a single piece of the mixture; and
identify the single piece of the mixture as a piece of glass with a label when the light transmittance boundary line is determined to be present on a single piece of the mixture.

18. The system of claim 17, wherein the processor is further configured to:
evaluate the position of an endpoint of the light transmittance boundary line on the outline to determine whether the light transmittance boundary line represents an intersection between two pieces of the mixture; and
identify the two pieces of the mixture as being a piece of glass and a piece of non-glass debris when the light transmittance boundary line is determined to represent an intersection between the two pieces of the mixture.

19. A non-transitory computer readable medium having a stored computer program embodying instructions, which when executed by a computer, causes the computer to evaluate a mixture including a plurality glass pieces, the computer readable medium comprising:

instructions to take an image of an object from the mixture, the object possibly being either a single piece from the mixture or at least two pieces from the mixture;
instructions to determine, from the image, angles of an outline of the object;
instructions to evaluate the angles to determine whether the object is at least two pieces;
instructions to evaluate a characteristic of the object;
instructions to detect, from the image, a light transmittance boundary line within the outline of the object, the light transmittance boundary line having an endpoint on the outline;
instructions to evaluate a position of an endpoint on the outline to determine whether the light transmittance boundary line is present on a single piece of the mixture; and
instructions to identify the single piece of the mixture as a piece of glass with a label when the light transmittance boundary line is determined to be present on a single piece of the mixture.

20. The non-transitory computer readable medium of claim 19, further comprising:
instructions to evaluate the position of an endpoint of the light transmittance boundary line on the outline to determine whether the light transmittance boundary line represents an intersection between two pieces of the mixture; and
instructions to identify the two pieces of the mixture as being a piece of glass and a piece of non-glass debris when the light transmittance boundary line is determined to represent an intersection between the two pieces of the mixture.

21. A system for evaluating a mixture including a plurality glass pieces, the system comprising:
an imaging device configured to take an image of an object from the mixture, the object possibly being either a single piece from the mixture or at least two pieces from the mixture;
a light source configured to direct light toward the imaging device; and
a processor configured to determining, from an image taken by the imaging device, angles of an outline of the object, the processor further configured to evaluate the angles to determine whether the object is at least two pieces and to evaluate a characteristic of the object,
wherein the processor is further configured to:
determine whether the mixture satisfies a predetermined requirement, wherein the predetermined requirement includes any one or both of a maximum amount of non-glass debris and a minimum amount glass having a desired color type; and
automatically change one or more parameters of a glass sorter from which the mixture was obtained, wherein the one or more parameters are changed based, at least, on a determination that the mixture obtained from the glass sorter does not satisfy the predetermined requirement.

22. A system for evaluating a mixture including a plurality glass pieces, the system comprising:
an imaging device configured to take an image of an object from the mixture, the object possibly being either a single piece from the mixture or at least two pieces from the mixture;
a light source configured to direct light toward the imaging device; and
a processor configured to determining, from an image taken by the imaging device, angles of an outline of the object, the processor further configured to evaluate the angles to determine whether the object is at least two pieces and to evaluate a characteristic of the object,
wherein the processor is further configured to:
determine whether the mixture satisfies a predetermined requirement, wherein the predetermined requirement includes any one or both of a maximum amount of non-glass debris and a minimum amount glass having a desired color type; and
automatically increase frequency of testing based, at least, on a determination that the mixture obtained from the glass sorter does not satisfy the predetermined requirement.

23. A non-transitory computer readable medium having a stored computer program embodying instructions, which when executed by a computer, causes the computer to evaluate a mixture including a plurality glass pieces, the computer readable medium comprising:
instructions to take an image of an object from the mixture, the object possibly being either a single piece from the mixture or at least two pieces from the mixture;
instructions to determine, from the image, angles of an outline of the object;
instructions to evaluate the angles to determine whether the object is at least two pieces;
instructions to evaluate a characteristic of the object;
instructions to determine whether the mixture satisfies a predetermined requirement, wherein the predetermined requirement includes any one or both of a maximum amount of non-glass debris and a minimum amount glass having a desired color type; and
instructions to automatically change one or more parameters of a glass sorter from which the mixture was obtained, wherein the one or more parameters are changed based, at least, on a determination that the mixture obtained from the glass sorter does not satisfy the predetermined requirement.

24. A non-transitory computer readable medium having a stored computer program embodying instructions, which when executed by a computer, causes the computer to evaluate a mixture including a plurality glass pieces, the computer readable medium comprising:
instructions to take an image of an object from the mixture, the object possibly being either a single piece from the mixture or at least two pieces from the mixture;
instructions to determine, from the image, angles of an outline of the object;
instructions to evaluate the angles to determine whether the object is at least two pieces;
instructions to evaluate a characteristic of the object;
instructions to determine whether the mixture satisfies a predetermined requirement, wherein the predetermined requirement includes any one or both of a maximum amount of non-glass debris and a minimum amount glass having a desired color type; and
instructions to automatically increase frequency of testing based, at least, on a determination that the mixture obtained from the glass sorter does not satisfy the predetermined requirement.

* * * * *